US007655717B2

(12) United States Patent
Goulbourne

(10) Patent No.: US 7,655,717 B2
(45) Date of Patent: Feb. 2, 2010

(54) OINTMENT COMPOSITION FOR TREATING DECUBITUS ULCERS AND METHODS FOR ITS MAKING AND ITS USE

(75) Inventor: Mary J. Goulbourne, 188-26 120th Rd., St. Albans, NY (US) 11412

(73) Assignee: Mary J. Goulbourne, Ocala, FL (US)

( * ) Notice: Subject to any disclaimer, the term of this patent is extended or adjusted under 35 U.S.C. 154(b) by 1661 days.

(21) Appl. No.: 10/197,941

(22) Filed: Jul. 17, 2002

(65) Prior Publication Data
US 2004/0013744 A1 Jan. 22, 2004

(51) Int. Cl.
*A61K 31/59* (2006.01)
*A61K 36/886* (2006.01)
*A61K 36/889* (2006.01)
*A61K 31/00* (2006.01)
*A61K 38/12* (2006.01)
*A61K 31/70* (2006.01)
*B65H 3/18* (2006.01)
*B60C 1/00* (2006.01)
*C10M 169/00* (2006.01)
*C10L 1/16* (2006.01)
*C11B 1/00* (2006.01)
*C08K 5/04* (2006.01)
*C10M 101/02* (2006.01)

(52) U.S. Cl. .................. 524/400; 424/744; 424/727; 424/555; 424/725; 508/120; 530/320; 530/319; 524/526; 514/1; 514/39; 554/8

(58) Field of Classification Search .................. None
See application file for complete search history.

(56) References Cited

U.S. PATENT DOCUMENTS

| 3,943,248 A | 3/1976 | Shulman |
| 4,005,191 A | 1/1977 | Clark |
| 4,330,527 A | 5/1982 | Arima et al. |
| 4,816,254 A | 3/1989 | Moss |
| 6,224,896 B1 | 5/2001 | Redmond |
| 6,419,963 B1 * | 7/2002 | Niazi .................. 424/757 |

OTHER PUBLICATIONS

Dematology Times (Jan. 1993) pp. 56.*

* cited by examiner

*Primary Examiner*—Christopher R Tate
*Assistant Examiner*—Amy L Clark

(57) ABSTRACT

An ointment composition for treating decubitus ulcers and methods for its making and its use. The composition includes a skin protestant ointment, a rash cream, an antibiotic ointment, virgin olive oil, and boric acid powder. The skin protestant ointment includes active ingredients petroleum 53.4%, lanolin 15.5%, and inactive ingredients cod liver oil containing vitamin A & vitamin D, a fragrance, light mineral oil, microcrystalline wax, and paraffin. The rash cream includes active ingredients dimethicone 1% and zinc oxide 10%, and inactive ingredients aloe barbadensis extract, benzyl alcohol, coconut oil, cod liver oil containing vitamin A & vitamin D, a fragrance, glycerol oleate, light mineral oil, ozokerite, paraffin, propylene glycol, sorbitol, synthetic beeswax, and water. The antibiotic ointment includes active ingredients polymyxin B sulfate 5,000 units, bacitracin zinc 400 units, and neomycin base (as sulfate) 3.5 mg., and an inactive ingredient white petroleum.

1 Claim, No Drawings

OINTMENT COMPOSITION FOR TREATING DECUBITUS ULCERS AND METHODS FOR ITS MAKING AND ITS USE

BACKGROUND OF THE INVENTION

1. Field of the Invention

The present invention relates to an ointment composition. More particularly, the present invention relates to an ointment composition for treating decubitus ulcers and methods for its making and its use.

2. Description of the Prior Art

Numerous innovations for compositions for treating skin irritations have been provided in the prior art that will be described. Even though these innovations may be suitable for the specific individual purposes to which they address, however, they differ from the present invention.

A FIRST EXAMPLE, U.S. Pat. No. 3,943,248 to Shulman teaches chemotherapeutic compositions and methods for topically traumatic, diseased and degenerative skin disorders. One of the invention compositions comprises abietic acid and a-tocopherol contained in a pharmaceutically acceptable carrier. One or more of the invention compositions are suitable for the alleviation of severe burn injuries, and in the treatment of other skin disorders such as diabetic ulcers, decubitus ulcers, gangrene, abrasions, lacerations, puncture wounds, localized infections, and the like.

A SECOND EXAMPLE, U.S. Pat. No. 4,005,191 to Clark teaches a topical ointment composition which includes a mixture of non-systemic bases comprising calcium carbonate, magnesium hydroxide, and aluminum hydroxide. The composition also includes an anhydrous lanolin base carrier material and a hydrophilic ointment base carrier material, and the ointment composition is effective to essentially adjust the acid-base balance at the area of topical application to a point which corresponds with normal healthy body tissue. The composition may further include a compound having pharmaceutically acceptable anesthetic properties. In addition to the topical ointment composition, a method is provided for treating skin injuries involving inflammation or destruction of tissue, such as decubitus ulcers, varicose ulcers and burns, which method involves preparing the above noted composition and applying it to the affected area.

A THIRD EXAMPLE, U.S. Pat. No. 4,330,527 to Arima et al. teaches a wound treatment agent which contains as an effective ingredient a fraction containing nucleoside phosphotransferase produced by a nucleoside phosphotransferase producing bacterium belonging to the genus Clostridium, solely or in combination with zinc oxide.

A FOURTH EXAMPLE, U.S. Pat. No. 4,816,254 to Moss teaches an ointment composition for treating skin irritations such as diaper rash and decubitus. The composition includes zinc oxide, boric acid, karaya gum, peruvian balsam, cod liver oil and an appropriate solvent and pharmaceutical carrier.

A FIFTH EXAMPLE, U.S. Pat. No. 6,224,896 to Redmond teaches a composition for use in the treatment of epidermal traumas. The composition comprises a nitroimadazole, an occlusive skin barrier composition, and an occlusive synthetic dressing. Furthermore, the invention comprises a method of treatment of the epidermal trauma using the novel composition.

It is apparent that numerous innovations for compositions for treating skin irritations have been provided in the prior art that are adapted to be used. Furthermore, even though these innovations may be suitable for the specific individual purposes to which they address, however, they would not be suitable for the purposes of the present invention as heretofore described.

SUMMARY OF THE INVENTION

ACCORDINGLY, AN OBJECT of the present invention is to provide an ointment composition for treating decubitus ulcers and methods for its making and its use that avoids the disadvantages of the prior art.

ANOTHER OBJECT of the present invention is to provide an ointment composition for treating decubitus ulcers and methods for its making and its use that is simple and inexpensive to manufacture.

STILL ANOTHER OBJECT of the present invention is to provide an ointment composition for treating decubitus ulcers and methods for its making and its use that is simple to use.

BRIEFLY STATED, STILL YET ANOTHER OBJECT of the present invention is to provide an ointment composition for treating decubitus ulcers and methods for its making and its use. The composition includes a skin protestant ointment, a rash cream, an antibiotic ointment, virgin olive oil, and boric acid powder. The skin protestant ointment includes active ingredients petroleum 53.4%, lanolin 15.5%, and inactive ingredients cod liver oil containing vitamin A & vitamin D, a fragrance, light mineral oil, microcrystalline wax, and paraffin. The rash cream includes active ingredients dimethicone 1% and zinc oxide 10%, and inactive ingredients aloe barbadensis extract, benzyl alcohol, coconut oil, cod liver oil containing vitamin A & vitamin D, a fragrance, glycerol oleate, light mineral oil, ozokerite, paraffin, propylene glycol, sorbitol, synthetic beeswax, and water. The antibiotic ointment includes active ingredients polymyxin B sulfate 5,000 units, bacitracin zinc 400 units, and neomycin base (as sulfate) 3.5 mg., and an inactive ingredient white petroleum.

The novel features which are considered characteristic of the present invention are set forth in the appended claims. The invention itself, however, both as to its construction and its method of operation, together with additional objects and advantages thereof, will be best understood from the following description of the specific embodiments when read and understood in connection with the accompanying drawing.

DESCRIPTION OF THE PREFERRED EMBODIMENT

The ointment composition of the present invention for treating decubitus ulcers comprises a skin protectant ointment, a rash cream, and an antibiotic ointment.

The ointment composition further comprises virgin olive oil and boric acid powder The skin protectant ointment comprises active ingredients and inactive ingredients. A typical such skin protectant ointment is sold under the tradename A+D OINTMENT, which is distributed by Schering-Plough HealthCare Products, Inc., Memphis, Tenn. 38151 USA).

The active ingredients of the skin protectant ointment comprise petroleum 53.4% and lanolin 15.5%.

The inactive ingredients of the skin protectant ointment comprise cod liver oil containing vitamin A & vitamin D, a fragrance, light mineral oil, microcrystalline wax, and paraffin.

The rash cream comprises active ingredients and inactive ingredients. A typical such rash cream is sold under the TRADENAME A+D ZINC OXIDE CREAM, which is distributed by Schering-Plough HealthCare Products, Inc., Memphis, Tenn. 38151 USA.

The active ingredients of the rash cream comprise dimethicone 1% and zinc oxide 10%.

The inactive ingredients of the rash cream comprise aloe barbadensis extract, benzyl alcohol, coconut oil, cod liver oil containing vitamin A & vitamin D, a fragrance, glyceryl oleate, light mineral oil, ozokerite, paraffin, propylene glycol, sorbitol, synthetic beeswax, and water.

The antibiotic ointment comprises active ingredients and an inactive ingredient. A typical such antibiotic ointment is sold under the tradename TRIPLE ANTIBIOTIC OINTMENT, which is distributed by Family Pharmacy, P.O. Box 1027, Southeastern, Pa. 19398-1027.

The active ingredients of the antibiotic ointment comprise polymyxin B Sulfate 5,000 units, bacitracin Zinc 400 units, and Neomycin Base (as Sulfate) 3.5 mg.

The inactive ingredient of the antibiotic ointment comprise white petroleum.

The method for making the ointment composition for treating decubitus ulcers comprises the steps of:

STEP 1: Mixing two (2) tablespoons of the virgin olive oil and two (2) tablespoons of the boric acid powder together so as to form a first composition.

STEP 2: Mixing the petroleum 53.4%, the lanolin 15.5%, the cod liver oil containing vitamin A & vitamin D, the fragrance, the light mineral oil, the microcrystalline wax, and the paraffin of the skin protectant ointment together so as to form a second composition.

STEP 3: Mixing the dimethicone 1%, the zinc oxide 10%, the aloe barbadensis extract, the benzyl alcohol, the coconut oil, the cod liver oil containing vitamin A & vitamin D, the fragrance, the glyceryl oleate, the light mineral oil, the ozokerite, the paraffin, the propylene glycol, the sorbitol, the synthetic beeswax, and the water of the skin rash cream so as to form a third composition.

STEP 4: Mixing the polymyxin B Sulfate 5,000 units, the bacitracin Zinc 400 units, the Neomycin Base (as Sulfate) 3.5 mg, and the white petroleum of the antibiotic ointment together so as to form a fourth composition.

STEP 5: Mixing two (2) tablespoons of the second composition, two (2) tablespoons of the third composition, and two (2) tablespoons of the fourth composition together so as to form a fifth composition.

STEP 6: Mixing the first composition and the fifth composition together 80 as to form the ointment composition for treating decubitus ulcers.

The method for using the ointment composition for treating decubitus ulcers comprises the steps of:

STEP 1: Cleaning the decubitus ulcers with hydrogen peroxide and letting air dry.

STEP 2: Applying the ointment composition to the decubitus ulcers twice a day until healed.

It will be understood that each of the elements described above, or two or more together, may also find a useful application in other types of constructions differing from the types described above.

While the invention has been illustrated and described as embodied in an ointment composition for treating decubitus ulcers, however, it is not limited to the details shown, since it will be understood that various omissions, modifications, substitutions and changes in the forms and details of the device illustrated and its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute characteristics of the generic or specific aspects of this invention.

The invention claimed is:

1. An ointment composition for treating decubitus ulcers comprising virgin olive oil, boric acid powder, white petroleum, lanolin, cod liver oil containing vitamin A and vitamin D, a fragrance, glyceryl oleate, light mineral oil, microcrystalline wax, paraffin, dimethicone, zinc oxide, aloe barbadensis extract, benzyl alcohol, coconut oil, ozokerite, propylene glycol, sorbitol, synthetic beeswax, water, polymyxin B Sulfate, bacitracin Zinc and Neomycin Base, whereby the ointment composition is obtained by a process comprising:

a.) mixing two (2) tablespoons of virgin olive oil with two (2) tablespoons of boric acid powder together to provide a first composition;

b.) mixing white petroleum in an amount of 53.4%, lanolin in an amount of 15.5%, cod liver oil containing vitamin A & vitamin D, fragrance, light mineral oil, microcrystalline wax, and paraffin together to provide a second composition in the form of a skin protectant ointment;

c.) mixing dimethicone in an amount of 1%, zinc oxide in an amount of 10%, aloe barbadensis extract, benzyl alcohol, coconut oil, cod liver oil containing vitamin A & vitamin D, a fragrance, glyceryl oleate, light mineral oil, ozokerite, paraffin, propylene glycol, sorbitol, synthetic beeswax, and water together to provide a third composition in the form of a skin rash cream;

d.) mixing polymyxin B sulfate in an amount of 5,000 units, bacitracin zinc in an amount of 400 units, neomycin Base (as sulfate) in an amount of 3.5 mg, and white petroleum together to provide a fourth composition; and e.) mixing two (2) tablespoons of the second composition with two (2) tablespoons of the third composition, and two (2) tablespoons of the fourth composition together to provide a fifth composition; and f.) mixing the first composition and the fifth composition together to provide said ointment composition.

* * * * *